US012765823B2

(12) United States Patent
Thelen et al.

(10) Patent No.: US 12,765,823 B2
(45) Date of Patent: Oct. 20, 2026

(54) WEARABLE MUSCLE TISSUE TENSIOMETER WITH BILATERAL WORK AND POWER MEASUREMENT

(71) Applicant: Wisconsin Alumni Research Foundation, Madison, WI (US)

(72) Inventors: Darryl Gerard Thelen, Madison, WI (US); Jack Anthony Martin, Madison, WI (US); Sara Elizabeth Harper, Madison, WI (US); Peter Gabriel Adamczyk, Madison, WI (US); Kelly Peregrine, Traverse City, MI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 316 days.

(21) Appl. No.: 18/291,274

(22) PCT Filed: Aug. 2, 2022

(86) PCT No.: PCT/US2022/039110
§ 371 (c)(1),
(2) Date: Jan. 23, 2024

(87) PCT Pub. No.: WO2023/018575
PCT Pub. Date: Feb. 16, 2023

(65) Prior Publication Data

US 2024/0374191 A1 Nov. 14, 2024

Related U.S. Application Data

(60) Provisional application No. 63/231,954, filed on Aug. 11, 2021.

(51) Int. Cl.
*A61B 5/22* (2006.01)
*A61B 5/00* (2006.01)
*G01L 5/04* (2006.01)

(52) U.S. Cl.
CPC ............ *A61B 5/221* (2013.01); *A61B 5/6833* (2013.01); *G01L 5/042* (2013.01); *A61B 2503/10* (2013.01); *A61B 2562/0219* (2013.01)

(58) Field of Classification Search
CPC ....................................................... A61B 5/221
See application file for complete search history.

(56) References Cited

U.S. PATENT DOCUMENTS

| | | | | |
|---|---|---|---|---|
| 10,631,760 | B2 * | 4/2020 | Dracup | A61B 5/4094 |
| 10,758,160 | B2 * | 9/2020 | Gong | A61B 5/6831 |
| 11,185,270 | B1 * | 11/2021 | Yang | A61B 5/1128 |
| 2005/0119568 | A1 | 6/2005 | Salcudean et al. | |
| 2006/0106313 | A1 | 5/2006 | Hobson | |

(Continued)

OTHER PUBLICATIONS

Daniel H. Cortes et al.; "Continuous shear wave elastography: a new method to measure viscoelastic properties of tendons in vivo." Ultrasound in medicine & biology 41, No. 6 (2015): pp. 1518-1529; US.

(Continued)

*Primary Examiner* — Eric S. McCall
(74) *Attorney, Agent, or Firm* — Boyle Fredrickson, S.C.

(57) ABSTRACT

A wearable tensiometer integrates patient-worn muscle tissue tensiometery and motion tracking to enable real-time energy measurement for an individual's full gait cycle outside of a laboratory environment.

16 Claims, 5 Drawing Sheets

(56) References Cited

U.S. PATENT DOCUMENTS

| | | | |
|---|---|---|---|
| 2009/0216119 | A1 | 8/2009 | Fan et al. |
| 2010/0286520 | A1 | 11/2010 | Hazard et al. |
| 2013/0317362 | A1 | 11/2013 | Shi et al. |
| 2014/0081136 | A1 | 3/2014 | Zhao et al. |
| 2015/0320394 | A1 | 11/2015 | Arnal et al. |
| 2017/0055836 | A1 | 3/2017 | Thelen et al. |
| 2019/0200900 | A1* | 7/2019 | Thelen ..................... A61B 8/42 |
| 2021/0007874 | A1* | 1/2021 | Galiana Bujanda .... A61F 5/028 |
| 2023/0052280 | A1* | 2/2023 | Martin ................. A61B 5/0057 |
| 2024/0180530 | A1* | 6/2024 | Thelen ..................... A61B 8/58 |
| 2024/0398380 | A1* | 12/2024 | Thelen ................... A61B 8/485 |

OTHER PUBLICATIONS

Sara E. Harper et al.; “Wearable Tendon Kinetics.” Sensors 20, No. 17 (2020): 4805; pp. 1-16; US.

* cited by examiner

WEARABLE MUSCLE TISSUE TENSIOMETER WITH BILATERAL WORK AND POWER MEASUREMENT

CROSS REFERENCE TO RELATED APPLICATION

This application claims the benefit of U.S. provisional application 63/231,954 filed Aug. 11, 2021, and hereby incorporated by reference.

STATEMENT REGARDING FEDERALLY SPONSORED RESEARCH OR DEVELOPMENT

--

BACKGROUND OF THE INVENTION

The present invention relates to an apparatus for measuring tendon and muscle tensions and in particular to a wearable device that can provide real-time tension and work measurements outside of the laboratory environment.

The measurement of tissue tension for muscles, muscle tissues, ligaments, and tendons (henceforth muscle tissue) has substantial value in the fields of orthopedics, athletics, rehabilitation, and ergonomics. Typically, such studies are done in a laboratory environment, for example, on a treadmill, and muscle tissue tension is deduced by making a measurement of force at a location on the limb removed from the muscle tissue against a force-sensing plate and then determining force on the muscle tissue by geometric calculation using quasistatic or dynamic biomechanical models. For example, a force against a pressure plate between the ball of the foot and the ground may be used to calculate a tension on the gastrocnemius muscle tissue by considering the effective lever arm of the foot pivoting about the ankle.

Such force calculations are subject to errors: in determination of the geometry of the limb necessary to determine force on the muscle tissue, in the influence of intervening structures between the force measurement and the tissue such as other muscles/tendons, ligaments, skin, bony joint limits, and clothing, and in converting force to actual tension. These errors can be compounded when measurements are conducted outside of a laboratory environment in varying environments such as with an individual walking over different elevational grades.

SUMMARY OF THE INVENTION

The present invention employs a patient-supported tensiometer that can directly measure muscle tissue tension and can be combined with patient-supported motion tracking to provide a wearable tensiometer that can provide real-time energy generation (e.g., power/work) measurements for particular muscle tissue. By eliminating the indirect measurements provided by force plates and the like, improved work and tension information can be provided in an outdoor environment in real time for more sophisticated studies and potentially biofeedback.

Specifically, the invention provides a kinetics monitoring system having at least one tensiometer attachable to an individual to measure tension of a muscle tissue and a motion tracker attachable to an individual to measure muscle tissue extension. An electronic computer communicating with the shear wave tensiometer and the motion tracker combines tension measures and the muscle tissue extension measures to provide an output indicating muscle tissue energy generation.

It is thus a feature of at least one embodiment of the invention to provide a wearable kinetics monitoring system that can provide work and/or power information through a combination of motion tracking and direct-major tension information allowing the system to be used both in the laboratory and outside of the laboratory.

The kinetics monitoring system may further include a housing holding the electronic computer and a power supply providing electrical power to the electronic computer, the tensiometer, and the motion tracker, the housing adapted to be supported on the individual.

It is thus a feature of at least one embodiment of the invention to provide a self-contained system that can be used untethered outside of the environment in a variety of different exercise scenarios.

The kinetics monitoring system may further include a wireless transmitter transmitting the output indicating muscle tissue energy generation.

It is thus a feature of at least one embodiment of the invention to allow remote monitoring of an individual and a reduction in individual carried weight by allowing remote processing.

The tensiometer may be a shear wave tensiometer deducing tension from a monitoring of shear wave speed through the muscle tissue. In some embodiments, the motion tracker may be an inertial motion tracker determining at least one of position, acceleration, and velocity through patient-supported inertial sensors.

It is thus a feature of at least one embodiment of the invention to provide tensiometers and motion tracking that can work in an untethered environment with sufficient accuracy to provide meaningful clinical information.

The kinetics monitoring system may further include a wearable display adapted to be supported on the individual to provide a display indicating muscle tissue associated work.

It is thus a feature of at least one embodiment of the invention to provide a system suitable for real-time biofeedback by an exercising individual.

In some embodiments, the kinetics monitoring system may include at least two tensiometers attachable to a left and right side limb of the individual to measure tension of muscle tissue, respectively, of the left and right side limbs, and the motion tracker may operate to separately determine a muscle tissue extension of the respective muscle tissue of the left and right side limbs. The electronic computer may then provide an output comparing muscle tissue associated energy usage for the left and right limbs.

It is thus a feature of at least one embodiment of the invention to provide insight into symmetry issues with respect to muscle energy usage, potentially providing important insights in athletics and rehabilitation beyond comparison to a normative value across individuals.

Similarly, in some embodiments, the kinetics monitoring system may include two tensiometers attachable to a first and second side of a joint of a limb of the individual and the motion tracker may operate to separately determine a muscle tissue extension of muscle tissue on the first and second sides of the limb. Here, the electronic computer provides an output comparing muscle tissue associated energy usage of the muscle tissue on the first and second sides of the limb.

It is thus a feature of at least one embodiment of the invention to provide insight into antagonistic muscle sets and work-sharing among those sets.

More generally, the shear wave tensiometers may be attached to first and second different muscle tissues and the motion tracker may operate to measure muscle tissue extension for the first and second different muscle tissues with the electronic computer providing an output indicating a time phase relationship between the energy generation of the first and second muscle tissues.

It is thus a feature of at least one embodiment of the invention to allow better quantification of the relative timing of muscle energy generation.

The tensiometer may include a flexible sheet supporting in separation a shear wave actuator for imparting a shear wave to a proximate muscle tissue and at least one shear wave sensor spaced from the shear wave actuator for measuring an arrival of the shear wave at the proximate sensor.

It is thus a feature of one embodiment of the invention to provide a mounting structure for the actuator and sensor that is flexible to allow conformance to an individual's limb while maintaining the spacing between components and providing good acoustic isolation to prevent "short-circuit" shear wave paths through the support.

The actuator and shear wave sensor may be separated along an axis, and the sheet may provide wings extending to a left and right side of the axis to wrap around a limb associated with the relevant muscle tissue.

It is thus a feature of at least one embodiment of the invention to provide a simple structure that both supports the sensor components and helps hold and position them against the limb.

In this regard, the wings may provide an adhesive material for fixing the wings to the limb.

It is thus a feature of at least one embodiment of the invention to simplify attachment of the shear wave tensiometer by providing stabilizing adhesive for initial positioning that may be sufficient alone or supplemented with elastic cuffs or the like.

In this regard, the flexible sheet may be anisotropic to stretch, under a given force, less in a direction of separation between the shear wave actuator and shear wave sensor and more in a direction perpendicular to the direction of separation between the shear wave actuator and shear wave sensor.

It is thus a feature of at least one embodiment of the invention to provide a bandage-like attachment with selective elasticity for retaining the transducers against the limb while preserving a constant transducer separation under stress.

An area of the sheet supporting the actuator and sensor between the wings may be free from adhesive material.

It is thus a feature of at least one embodiment to eliminate adhesive-induced shear wave coupling between the muscle tissue and the support sheet.

These particular objects and advantages may apply to only some embodiments falling within the claims and thus do not define the scope of the invention.

DETAILED DESCRIPTION OF THE PREFERRED EMBODIMENT

Figure 1:
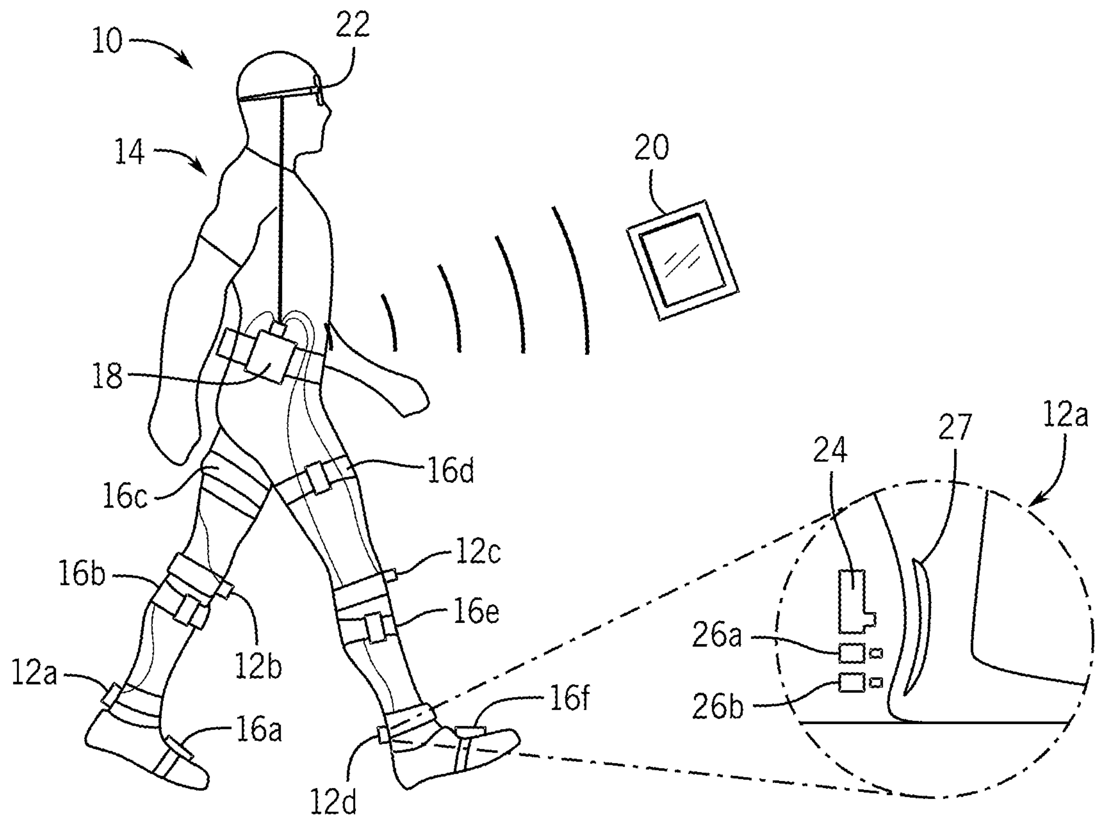
FIG. 1 is a simplified representation of a walking individual instrumented according to the present invention to include multiple shear wave tensiometers and inertial measurement units to allow tension and work measurement outside of a laboratory environment on the left and right sides of an individual.

Referring now to FIG. 1, a kinetics monitoring system 10 according to the present invention may provide for multiple tensiometers 12*a*-12*d* positioned to measure muscle tissues of interest on an individual 14, for example, during walking, running, or other exercise. For example, tensiometers 12*a* and 12*d* may be positioned near the individual's ankles to measure the tension on the Achilles tendon (gastrocnemius and/or soleus muscle) of the left and right legs, respectively, and tensiometers 12*b* and 12*c* may be positioned slightly below the individual's kneecaps to measure the tension on the patellar tendon associated with the quadriceps muscle of the individual's legs.

The kinetics monitoring system 10 may also provide for motion tracking elements 16*a*-16*f* providing measurements of the relative angulation between the individual's foot and lower leg and relative angulation between the individual's thigh and lower leg for both the left and right leg and thus provide an indication of muscle extensions about the ankle and knee, respectively.

Each of the tensiometers 12 and motion tracking elements 16 may communicate with a waist-supported control unit 18 providing wireless communication with a tablet 20 or the like which may be monitored by a second individual, and/or with a user interface 22, for example, augmented reality glasses that can be worn by the individual 14, aural coaching from the individual using the tablet 20, sonification of signals so they can be heard by the individual, vibrotactile feedback, or the like. The invention contemplates that the tensiometers 12 and motion tracking elements 16 may alternatively communicate directly with the remote device such as tablet 20 or a smart phone or the like.

The motion tracking elements 16, for example, may be held on the individual 14 by elastic straps joined with hook and loop fasteners about legs of the individual 14. In one embodiment the motion tracking elements 16 are inertial measurement units (IMU's) commercially available under the trade name MVN Awinda from XSens B. V. of the Netherlands. Such motion tracking elements 16 may provide for three-axis absolute angular orientation measurements using a 3-D rate gyroscope, a 3-D accelerometer, a 3-D magnetometer, and software to allow extraction of the relative angular measurements. Each of the motion tracking elements 16 may provide for multiple signals including those associated with the sensors described above through the interface circuit 32 to the microcontroller 34.

Alternatively, the motion tracking may be provided by a camera system observing the individual using motion capture techniques or software extraction, for example, described in Zhe Cao, "OpenPose: Real-Time Multi-person 2D Pose Estimation Using Part Affinity Fields" arXiv: 1812.08008v2 [cs.CV] 30 May 2019 or through the use of electrogoniometers or the like such as are commercially available from Biometrics Limited of Newport United Kingdom.

The tensiometers 12 may be shear wave tensiometers (SWT) providing a measurement of shear wave velocity through the muscle tissue as discussed generally in US patent application 2017/0055836, assigned to the present assignee and hereby incorporated by reference. In such a design, an actuator 24 is positioned along a longitudinal extent of a muscle tissue 27 to induce a shear wave through the muscle tissue 27 which may be received by a first and second shear wave sensor 26*a* and 26*b* to measure the shear wave velocity to deduce tension.

Figure 2:
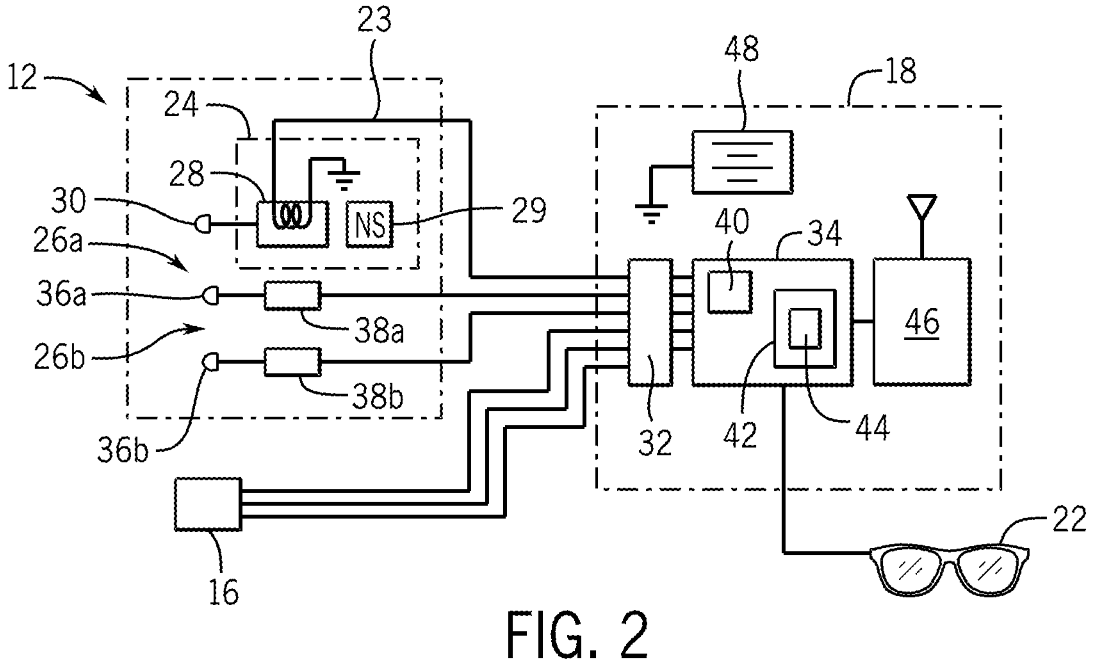
FIG. 2 is a simplified schematic of the system of FIG. 1 also providing telemetry and biofeedback.

Referring now to FIG. 2, the actuator 24 may make use of a voice coil driver 23 of the type employing a movable current-carrying coil 28 communicating with an actuator head 30, the latter positioned against the muscle tissue 27 and moving under the influence of a magnetic field generated by magnet 29. An actuating signal providing current to the coil 28 may be received from an interface circuit 32 in the control unit 18, for example, the latter providing a necessary amplifier controlled by a microcontroller 34. Alternatively the voice coil can be replaced with a piezoelectric actuator stack, for example, commercially available under the tradename PK4JQP2, from Thorlabs, Newton, NJ, USA.

Each of the tensiometers 12 may provide a sensing contact head 36*a* and 36*b* communicating with a corresponding accelerometer 38*a* and 38*b*, the latter also providing signals through interface circuit 32 with microcontroller 34. Accelerometers suitable for this purpose are available under the trade name Model 352C23 from PCB Piezotronics, Depew, NY, USA. Alternative devices and sources include accelerometers manufactured under the tradename of ADXL 1002 and available from Analog Devices Inc., or under the tradename IIS3DWB and available from ST Microelectronics. Each of the tensiometers 12 may provide a signal through the interface circuit 32 to the microcontroller 34.

The microcontroller 34 may have one or more processors 40 communicating with electronic memory 42 holding a stored program 44 as will be discussed below. In addition, the microcontroller 34 may communicate with a wireless transmission unit 46 (for example, a Bluetooth or Wi-Fi communication circuit) allowing communication with tablet 20 as described above. An additional interface allows communication with the user interface 22. The control unit 18 may have a self-contained battery 48 allowing the entire kinetics monitoring system 10 to be untethered for use outside of laboratory.

Figure 3:
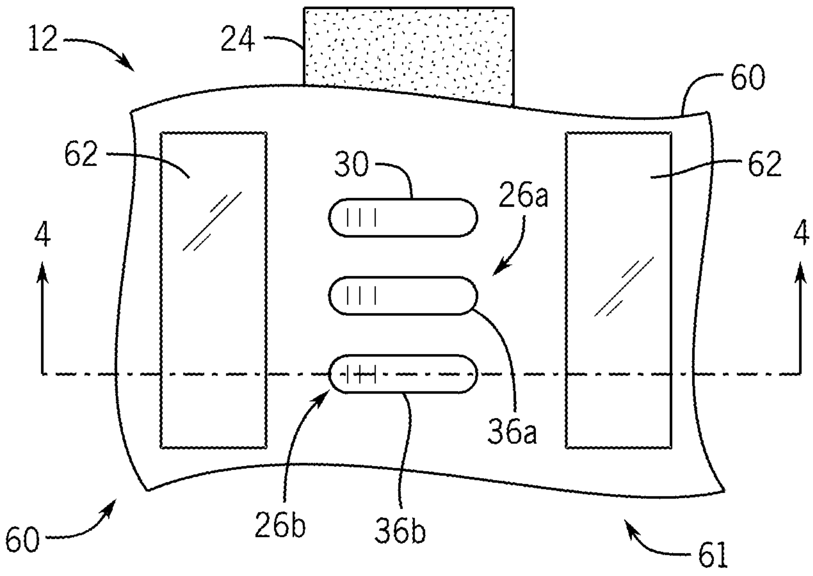
FIG. 3 is a front elevational view of an individual-contacting side of a shear wave tensiometer showing a floating support of two accelerometers and an actuator in a sound dampening flexible sheet.

Referring now to FIG. 3, each of the tensiometers 12 may be fabricated using an elastomeric sheet 60 that may flexibly be wrapped around the limb of the individual 14 and which supports in floating fashion each of the actuator 24 and the sensors 26*a* and 26*b*. This mounting system isolates the elements of the actuator 24 and sensors 26 which physically communicate only through the material of the sheet 60 and the muscle tissue 27 and overlying body tissue such as skin or connective, adipose tissue. In this respect, the sheet 60 provides vibration isolation to damp acoustic communication through the sheet 60. In one embodiment, the sheet 60 may be a sound-dampening material commercially available under the tradename of Sorbothane 101 from Sorbothane Incorporated of Canton, Ohio. In one embodiment the sheet 60 may have a 40 durometer (Shore 00) and a rebound height of less than 27% and desirably less than 12% and in some cases less than 5% as measured by ASTM D 2632-92. The invention contemplates that the sheet 60 has high stiffness in the axial direction so the distances stay constant but low shear stiffness so they can move relative to each other in a transverse plane. Alternatively, or in addition, the material may be anisotropic with respect to elasticity, having relatively low elasticity along the separation axes of the sensors 26 and actuator head 30, and higher elasticity perpendicularly to wrap around the limb.

The sheet 60 may not only support the actuator 24 and sensors 26 with respect to each other but also with respect to a limb of the individual 14. For this purpose, in one example, the sheet 60 may have a dimension of 5 cm along the limb axis and 10 cm circumferentially about the limb axis and be 0.125 inches in thickness.

Figure 4:
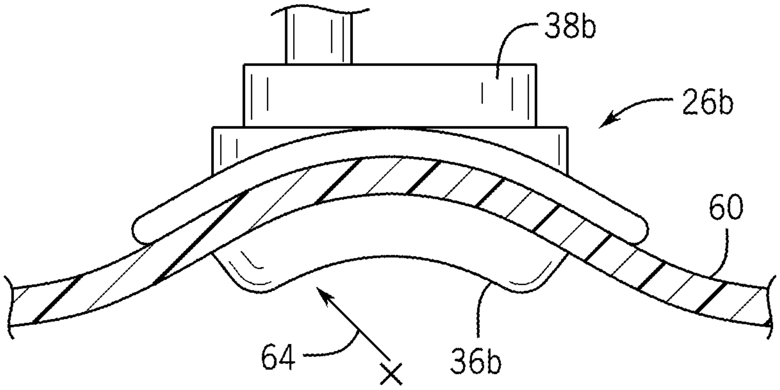
FIG. 4 is a cross-sectional view through one accelerometer of FIG. 2 along line 3-3 showing a conformal patient-contacting surface for improved coupling to muscle tissue.

Referring to FIGS. 2, 3 and 4, the driver 23 of the actuator 24 and the accelerometers 38 of the sensors 26*a* and 26 may be mounted on an outside of the sheet 60 with the actuator contact head 30 and sensor contact heads 36 protruding through the sheet 60 toward the individual 14 when in use. Left and right wings 61 of the interior of the sheet 60 flanking the heads 30 and 36 may include a pressure-sensitive adhesive material 62 allowing attachment to the individual's leg and in close contact therewith. In some embodiments, each wing 61 may be bifurcated as in a butterfly bandage. A portion of the sheet 60 between the left and right wing 61 may be free from pressure-sensitive adhesive to reduce acoustic coupling between the sheet 60 and the individual 14 outside of the regions of the contact heads 30 and contact heads 36. Each of the contact heads 30 and contact heads 36 may provide for an outwardly concave surface (facing the individual 14) having a radius 64 to match the approximate radius of the desired anatomy of a standard (or specific) individual for improved acoustic coupling. Generally, the contact heads 30 and contact heads 36 will be a rigid, hard thermoplastic material for good acoustic transmission without damping.

It will be appreciated the material of the sheet 60 not only serves to isolate vibration between the actuator 24 and the sensors 26*a* and 26*b* while providing flexibility allowing close conformance with the limb of the individual 14, but otherwise has relatively low elasticity so as to provide an accurate dimensional separation between the components of the actuator 24 and the sensors 26 under normally applied tensions.

Figure 5:
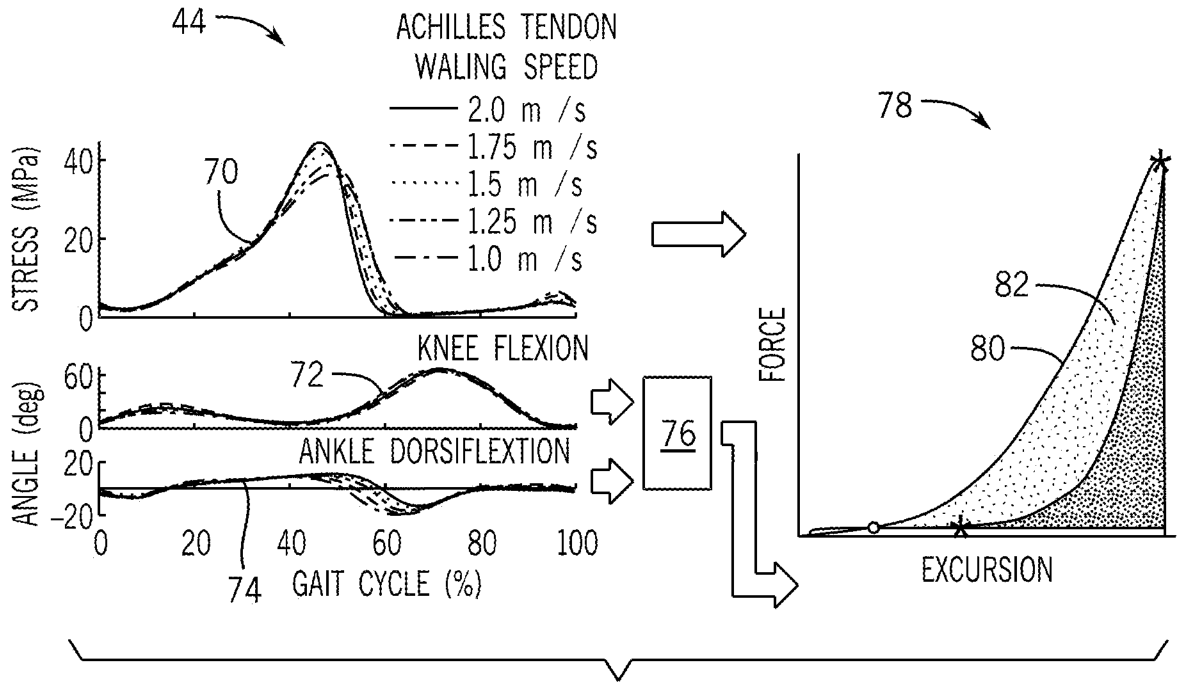
FIG. 5 is a representation of data collected by the circuitry of FIG. 4 to present measurements of stress and joint angle, which are converted to muscle tissue tension and excursion to provide a work loop indicating that work over a gait cycle.

Referring now to FIGS. 2 and 5, the program 44 of the microcontroller 34 may provide for the microcontroller 34 to collect a sampling of data from each of the accelerometers

38 and motion tracking elements 16 after each excitation of the actuator 24, the latter providing a shear wave stimulus to the muscle tissue 27 to obtain multiple sample points throughout a movement cycle of the individual. The sample points may be synchronized in time through one of a variety of means including the transmission of a simultaneous sample signal to each of the actuator 24, accelerometers 38, and motion tracking elements 16 or the use of a master synchronized clock as is generally understood in the art. The synchronization signal may be also provided to other sensors that may be collecting information about the individual including, for example, heartbeat sensors, respiration sensors, electromyographic sensors, and other known physiological sensors, including force plates and instrumented treadmills. Each sample may be identified to a time or a location (percentage) of the movement cycle, for example, as keyed from a foot strike sensor in gait (not shown) or deduced by analysis of the collected data revealing a movement pattern.

Per the sampling, each of the sensors 26 may provide for a stress waveform 70 over the gait cycle, and each pair of motion tracking elements 16 may provide for a muscle tissue extension measurement, for example, yielding a knee flexion signal 72 and an ankle dorsiflexion signal 74 per the embodiment of FIG. 1. The stress waveform 70 may be deduced from shear wave speed measured by the tensiometers 12 through a calibration process where a known force is applied to a limb and the resulting force 72 on the muscle tissue may be deduced by inverse dynamics considering a lever arm between a location of the force and effective pivot points, etc. These measurements, which may be conducted in a laboratory environment or in the field, are then used to produce a calibration that can be used in the field. An alternative method of calibrating the tensiometers 12 is described in co-pending application 63/231,566 filed Aug. 10, 2021, hereby incorporated by reference.

The stress signals 72 and 74 may be processed by the program 44 using a geometric, quasi-static or dynamic model 76 to yield, for each leg and for each muscle tissue 27 of interest, a work cycle 78 plotting tension on the muscle tissue (e.g., the gastrocnemius) versus extension or excursion of the muscle tissue 27 on the horizontal axis to provide a force loop 80.

In cases where the muscle tissue force is distributed across the distinct muscle tissues, for example, with Achilles forces shared by the gastrocnemius and soleus, the force may be apportioned according to a physiological cross-sectional area of the muscle, for example, with 65% of the force attributed to the soleus and the remaining 35% attributed to the gastrocnemius, such as may be obtained either by normative data or subject measurements. Alternatively, the apportionment may be according to measured electromyographic activity, or according to a musculoskeletal model, or according to other assumptions or models or any combination of these.

The area 82 within the force loop 80 indicates net work done by the muscle tissue 27 and is obtained by subtracting from the positive work defined by the upper surface of the loop 80 and its area downward to the horizontal axis, the negative work defined by the lower surface of the loop 80 and its area downward to the horizontal axis. Each point on the loop 80 may be mapped to a particular location in the movement cycle and the loop 80 repeats for each movement cycle providing a slightly different shape and different values of work.

Figure 6A:
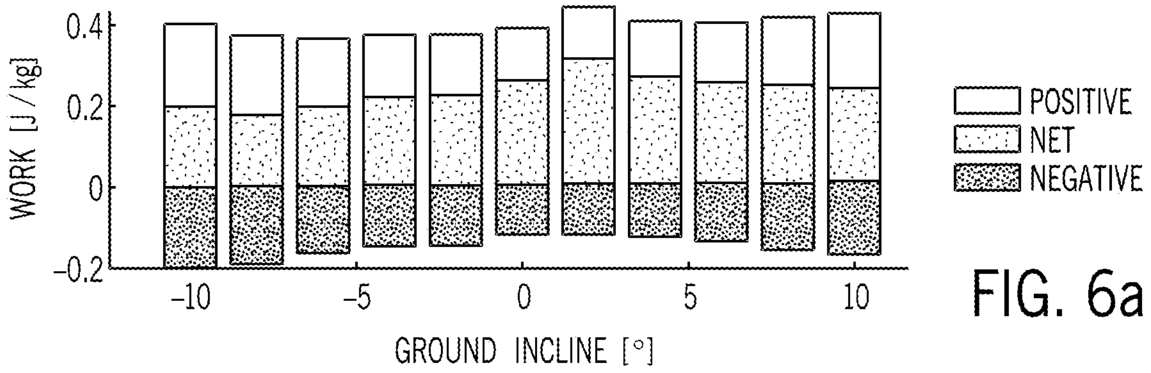
FIGS. 6*a* and 6*b* are outputs indicating work for different ground incline levels such as may be used in an outdoor environment to assess work burden in a varying environment.
Figure 6B:
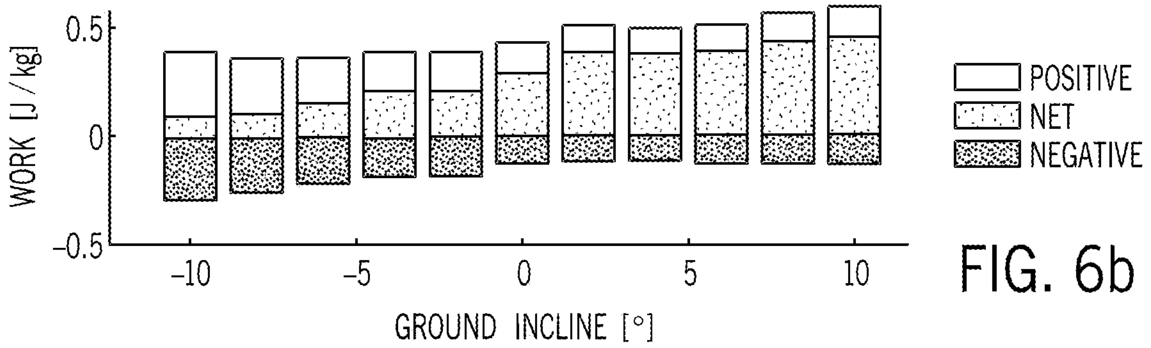

Referring now to FIG. 6*a*, the data of the work cycle 78 may be used to provide a indication of positive, net, and negative work or power for a particular muscle tissue 27, for example, the gastrocnemius as shown, for example, as an individual 14 walks or runs over terrain having different grades to provide a real-time indication of exertion, biomechanical loading, and power output. As shown in FIG. 6*b*, similar data can be provided for other muscle groups including, for example, the soleus, by shifting the location of the SWT 12 appropriately and making assumptions about how the Achilles tendon force is distributed between these two muscles as discussed above.

Figure 7:
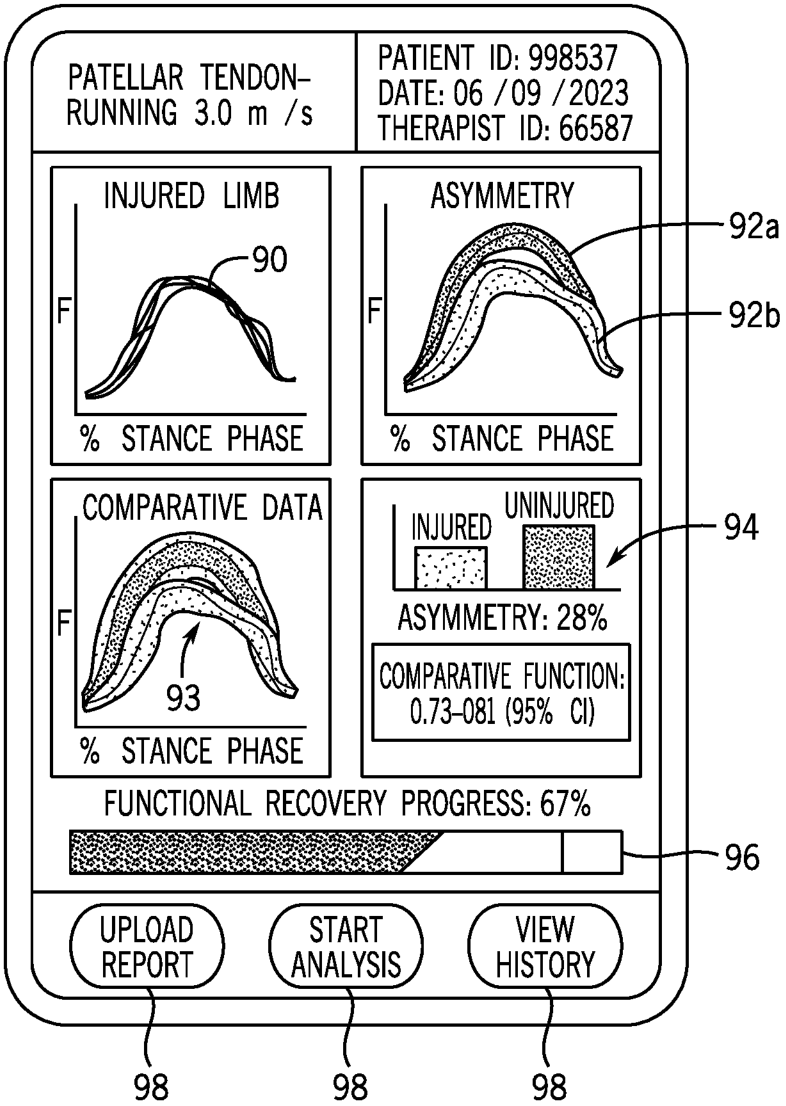
FIG. 7 is a comparison of a left limb to a right limb with respect to work measures such as can provide insight into asymmetry in kinetics by an individual.

Referring now to FIG. 7, the ability to instrument both the left and right limbs allows the outputting of data comparing these two limbs. In this example, an individual may have had ACL (anterior cruciate ligament) reconstruction surgery on their right knee and a rehabilitation goal of achieving peak patellar tendon loading with less than 10% asymmetry between injured and uninjured limbs, and within one standard deviation of the comparative population mean. The display, for example on the tablet 20 or on the user interface 22, may show tendon loading data 90 from a current test on the injured limb, bilateral tendon loading data 92*a* and 92*b* respectively for each limb, and loading on the injured limb in comparison to the statistical distribution of an appropriate comparison population 93. Each of these load measurements may be plotted over a gait cycle or movement cycle. Summary metrics 94 show quantitative asymmetry evaluation and function in comparison to the population norm. A progress indicator 96 uses the individual's test history to indicate how far they have advanced toward their goal since their first session. Additional user controls 98 allow convenient access to additional functions such as history and report generation.

Figure 8:
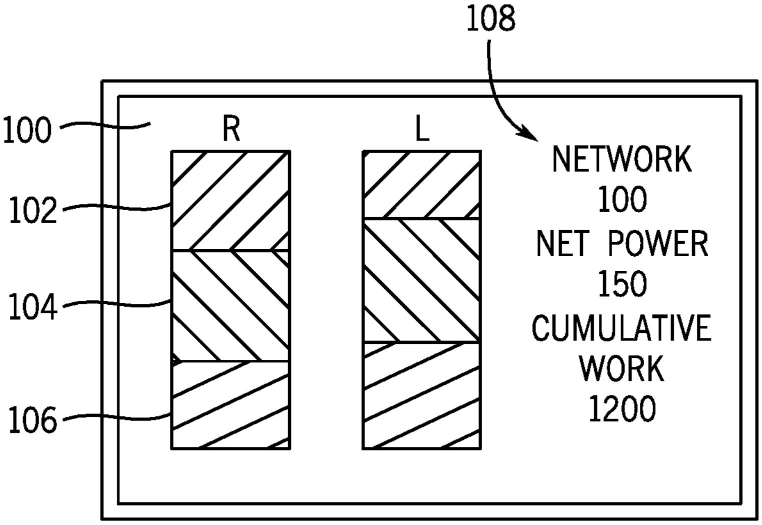
FIG. 8 is an example display that may be provided to the individual showing variations in work measures for left and right limbs and providing quantitative outputs of net work, net power, and cumulative work such as may be useful in monitoring an individual's exertion.

Referring now to FIG. 8, the individual 14 may also be provided with a summary screen 100, for example, providing measurements of positive work 102, net work 104, and negative work 106 for a muscle of interest on each of the right and left legs, together with quantitative information 108, for example, the quantitative measurement of net work, a quantitative peak power measurement, as well as other measurements including total work for a given training interval. Other measurements include impulse on a given muscle-tendon over time, minimum and maximum force on each limb and timing of peak power within the movement cycle. Generally, both work and power measurements can be derived and displayed from the same data using, for example, muscle extension information and differentiating that to get velocity which times tension provides a real-time power measurement.

Figure 9:
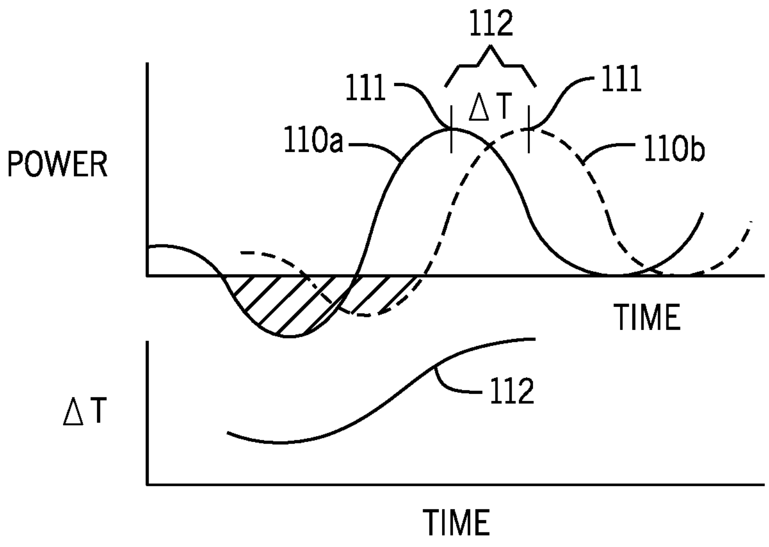
FIG. 9 is an example display showing the timing of energy usage for two different muscle tissue groups on a first time scale and a separation between peak energy generation over a second time scale.

Referring now to FIG. 9, a plot of work or power 110*a* and 110*b* for a first and second muscle tissue, for example, associated with the knee and ankle respectively, may be obtained with respect to time. This information may be used to establish a time delay 112 (or phase delay with respect to gait) between peak energy usage of these muscle tissues, for example, between peak power points 111 on the plots 110*a* and 110*b* during an individual's walking or running or performing other activities such as jumping or landing. This time delay 112 may also be plotted against time to show its evolution during an activity, for example, during which walking or running pace is changed or where the individual is traveling up or down a hill. This time-domain information can provide important insight into the sequential activation of muscle groups and load sharing.

Figure 10:
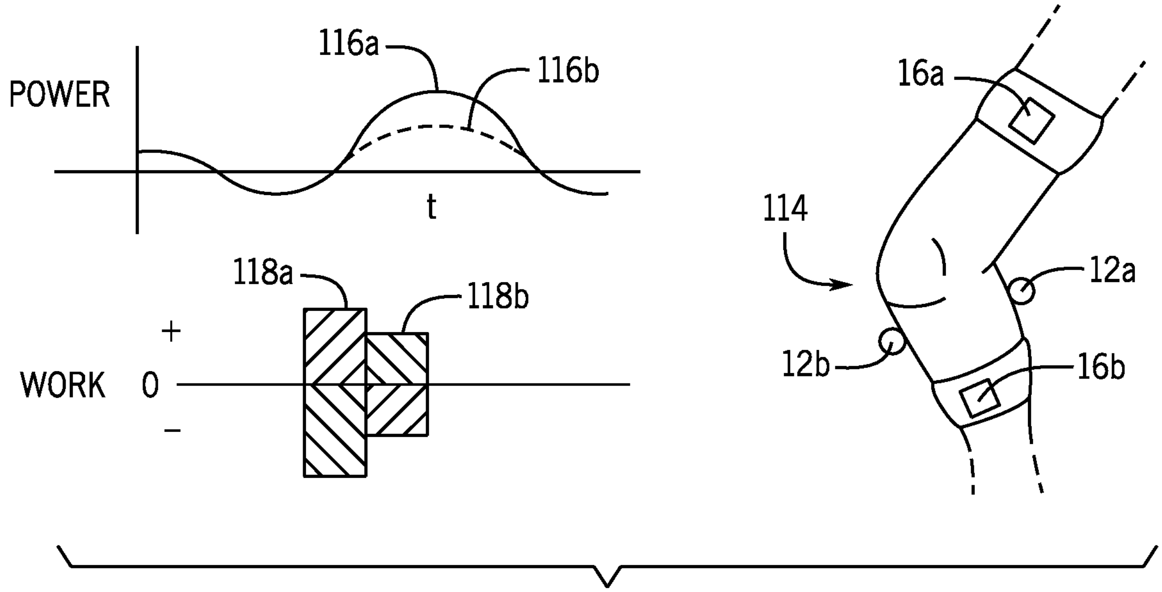
FIG. 10 is a set of figures showing placement of tensiometers and motion tracking elements on opposite sides of a joint in a limb to measure antagonistic forces on the joint and such as may be useful in monitoring muscle and movement coordination.

Referring now to FIG. 10, in contrast to the bilateral measurements discussed above with respect to FIG. 8, tensiometers 12*a* and 12*b* and motion tracking elements 16*a* and 16*b* may be placed on opposite sides of a joint, such as on the front and back of the knee joint 114 (or ankle joint, not shown), to monitor symmetry (or asymmetry) in energy usage in opposition or antagonistically in muscle tissue across the joint 114. In this case, for example, muscle tissue power 116*a* and 116*b* for muscle tissue in the front and back of the joint 114 may be plotted and displayed as a function of time showing periods of net positive and negative power. In addition, a bar-chart display similar to that shown in FIG. 8 may be created, for example, denoting cumulative work 118*a* and 118*b* both in the positive and negative domains for the two different muscle tissues above and below the joint 114. When muscles are in an agonist-antagonist relationship, co-contraction can be assessed in this manner. Co-contraction is inefficient energetically, but can be useful for stabilizing the joint, and thus provides important insight.

The present application incorporates by reference US patent application 2017/0055836, entitled: Apparatus for Dynamic Stress Measurement, US Patent Application and Harper S E, Roembke R A, Zunker J D, Thelen D G, Adamczyk P G, "Wearable Tendon Kinetics", sensors (Basel). 2020; 20 (17): 4805, published 2020 Aug. 26, doi: 10.3390/s20174805 and S. E. Harper, D. G. Schmitz, P. G. Adamczyk, and D. G. Thelen, "Fusion of Wearable Kinetic and Kinematic Sensors to Estimate Triceps Surae Work during Outdoor Locomotion on Slopes," Sensors, vol. 22, no. 4, Art. no. 4, 2022, doi: 10.3390/s22041589.

While a specific example of the invention has been provided, the invention contemplates use with a variety of different muscles/tendons (alone or in combination) including but not limited to: biceps femoris (hamstrings); medial and/or lateral hamstring tendons (behind the knee, inside and outside); tibialis anterior—TA tendon (front of ankle); wrist flexors—inside of wrist; finger extensors—back of hand; biceps brachii—inside of elbow; toe extensors—top of forefoot; triceps brachii—above elbow, on dorsal side (outside); and the combination of the patellar tendon and both medial and lateral hamstrings.

The above embodiment describes the use of two sensors 26; however, it will be appreciated that the invention also contemplates use of a single sensor and a detection of actuation of the actuator head 30 for time measurement.

It is contemplated that the various embodiments described above may be combined, for example, to make bilateral measurements and measurements above and below given joints at the same time, or conversely, a single side the joint of the individual may be measured. It should be understood that the present invention and the various embodiments may flexibly present data related to energy usage in various forms, for example, as a power or work measurement and as derivatives of power and integrations of work, etc. Measurements of work or power and similar measurements derived from these measurements of energy will be generally termed energy usage herein. Each of the various plots and displays described above may be obtained in a variety of different activities by the individual including walking, running, jumping, and landing from a jump.

Certain terminology is used herein for purposes of reference only, and thus is not intended to be limiting. As noted, "muscle tissue" refers collectively to any of muscles tendons or ligaments associated with work measurements. The terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order or quantity unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microcontroller and "a computer" or the like can be understood to include one or more microprocessors that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A kinetics monitoring system comprising:

a tensiometer attachable to an individual to provide a measure of muscle tension of a muscle tissue over a period of time of muscle exercise;

a motion tracker attachable to an individual to provide a measure of muscle tissue extension during the period of time of muscle exercise; and an electronic computer communicating with the tensiometer and the motion tracker to combine the measure of muscle tension and the measure of muscle tissue extension to provide an output indicating muscle tissue energy usage based on an area under a curve described by the measure of muscle tension as a function of the measure of muscle tissue extension.

2. The kinetics monitoring system of claim 1 further including a housing holding the electronic computer and holding a power supply providing electrical power to the electronic computer, the tensiometer and the motion tracker, the housing adapted to be supported on the individual.

3. The kinetics monitoring system of claim 1 further including a wireless transmitter transmitting the output indicating muscle tissue energy usage.

4. The kinetics monitoring system of claim 1 wherein the motion tracker is an inertial motion tracker determining at least one of position, acceleration, and velocity through patient-supported inertial sensors.

5. The kinetics monitoring system of claim 1 further including a wearable display adapted to be supported on the individual to provide a display indicating muscle tissue energy usage.

6. The kinetics monitoring system of claim 1 wherein the computer includes an anatomical model relating motion of the individual to muscle extension.

7. The kinetics monitoring system of claim 1 wherein the energy usage is selected from at least one of work and power.

8. A kinetics monitoring system comprising:

a tensiometer attachable to an individual to measure tension of a muscle tissue;

a motion tracker attachable to an individual to measure muscle tissue extension; and an electronic computer communicating with the tensiometer and the motion tracker to combine tension measures and the muscle tissue extension measures to provide outputs indicating muscle tissue energy usage; and wherein the tensiometer is a shear wave tensiometer deducing tension from a monitoring of shear wave speed through the muscle tissue.

9. A kinetics monitoring system comprising:

a tensiometer attachable to an individual to measure tension of a muscle tissue;

a motion tracker attachable to an individual to measure muscle tissue extension; and an electronic computer communicating with the tensiometer and the motion tracker to combine tension measures and the muscle tissue extension measures to provide outputs indicating muscle tissue energy usage; and further including at least two tensiometers attachable to a left and right side limb of the individual to measure tension of muscle tissue, respectively, of the left and right side limbs and wherein the motion tracker operates to separately determine a muscle tissue extension of the respective muscle tissue of the left and right side limbs and wherein the electronic computer provides an output comparing muscle tissue associated energy usage for the left and right limbs.

10. A kinetics monitoring system comprising:

a tensiometer attachable to an individual to measure tension of a muscle tissue;

a motion tracker attachable to an individual to measure muscle tissue extension; and an electronic computer communicating with the tensiometer and the motion tracker to combine tension measures and the muscle tissue extension measures to provide outputs indicating muscle tissue energy usage; and further including at least two tensiometers attachable to a first and second side of a joint of a limb of the individual and wherein the motion tracker operates to separately determine a muscle tissue extension of muscle tissue on the first and second sides of the limb and wherein the electronic computer provides an output comparing muscle tissue associated energy usage of the muscle tissue on the first and second sides of the limb.

11. A kinetics monitoring system comprising:

a tensiometer attachable to an individual to measure tension of a muscle tissue;

a motion tracker attachable to an individual to measure muscle tissue extension; and an electronic computer communicating with the tensiometer and the motion tracker to combine tension measures and the muscle tissue extension measures to provide outputs indicating muscle tissue energy usage; and further including at least two tensiometers attachable, respectively, to first and second different muscle tissues and wherein the motion tracker operates to measure muscle tissue extension for the first and second different muscle tissues and wherein the electronic computer provides an output indicating a time phase relationship between the energy usage of the first and second muscle tissues.

12. A kinetics monitoring system comprising:

a tensiometer attachable to an individual to measure tension of a muscle tissue;

a motion tracker attachable to an individual to measure muscle tissue extension; and an electronic computer communicating with the tensiometer and the motion tracker to combine tension measures and the muscle tissue extension measures to provide outputs indicating muscle tissue energy usage; and wherein the tensiometer includes a flexible sheet supporting in separation a shear wave actuator for imparting a shear wave to a proximate muscle tissue and at least one shear wave sensor spaced from the shear wave actuator for measuring an arrival of the shear wave at the proximate sensor.

13. The kinetics monitoring system of claim 12 wherein the shear wave actuator and shear wave sensor are separated along an axis, and the flexible sheet provides wings extending to left and right sides of the axis to wrap around a limb of the muscle tissue.

14. The kinetics monitoring system of claim 13 wherein the wings provide an adhesive material for fixing the wings to the limb.

15. The kinetics monitoring system of claim 13 wherein an area of the flexible sheet supporting the actuator and sensor between the wings is free from adhesive material.

16. The kinetics monitoring system of claim 13 wherein the flexible sheet is anisotropic to stretch, under a given force, less in a direction of separation between the shear wave actuator and shear wave sensor and more in a direction perpendicular to the direction of separation between the shear wave actuator and shear wave sensor.

* * * * *